United States Patent [19]

Edgren

[11] Patent Number: 4,519,801
[45] Date of Patent: May 28, 1985

[54] OSMOTIC DEVICE WITH WALL COMPRISING CELLULOSE ETHER AND PERMEABILITY ENHANCER

[75] Inventor: David Edgren, El Granada, Calif.

[73] Assignee: ALZA Corporation, Palo Alto, Calif.

[21] Appl. No.: 397,517

[22] Filed: Jul. 12, 1982

[51] Int. Cl.³ .............................................. A61K 9/22
[52] U.S. Cl. .................................. 604/892; 604/890; 424/19; 424/31; 424/32
[58] Field of Search ................................. 604/890–893; 424/DIG. 7, 19–21, 16, 31, 32; 427/2, 3, 245; 210/655, 654, 500.2; 106/197 R, 197 C, 169, 179

[56] References Cited

U.S. PATENT DOCUMENTS 2,958,656 11/1960 Stuckey .............................. 210/655
3,845,770 11/1974 Theeuwes et al. .................. 604/893
4,051,040 9/1977 Hazdra et al. ..................... 210/500.2
4,171,987 10/1979 Horiguchi et al. ................ 106/197.1

OTHER PUBLICATIONS

Cont. Rel. Tab., Walton et al., Chemical Abstracts, vol. 87, 1977, p. 381, 87:11647p.
Folic Acid Animal Feed Materials, Harte et al., Chem. Abs., vol. 89, 1978, p. 409, 89:89136g.
Opt. Use of Cell. as Adj. in Mix. with the Aid of Reg. Mode., Moldenhauer et al., Chem. Abs., vol. 89, 1978, p. 361, 89:152646r.
Sus. Rel. of Drugs from Et. Cell.–Polyet. Gly. Films and Kin. of Drug Rel., Samuelov et al., Chem. Abs., vol. 90, 1979, p. 390, 90:174620a.
Reverse Osmosis w. Dyn. Formed Mem. from Wat. Sol. Poly.; Igawa et al.; J. App. Poly. Sci., vol. 22; 1607–1618; 6/1978.
Zero Order Drug del., Donbrow et al., J. Pharm. Phar., 1980, vol. 32, pp. 463–470.
Cont. Rel. Tab., Weiss et al., Chem. Abs., vol. 94, 1981, p. 393, 94:214631w.

Primary Examiner—Richard J. Apley
Assistant Examiner—Gregory Beaucage
Attorney, Agent, or Firm—Paul L. Sabatine; Edward L. Mandell; Steven F. Stone

[57] ABSTRACT

An osmotic delivery system is disclosed for dispensing a useful agent. The system comprises a semipermeable wall surrounding a compartment housing the agent. The wall comprises a cellulose ether, an organic solvent soluble polymer, and optionally an aqueous soluble polymer. A passageway in the wall connects the interior of the system with the exterior for dispensing an agent from the system.

9 Claims, 5 Drawing Figures

OSMOTIC DEVICE WITH WALL COMPRISING CELLULOSE ETHER AND PERMEABILITY ENHANCER

FIELD OF THE INVENTION

This invention pertains to an osmotic device. More particularly, the invention relates to an osmotic dispensing device comprising, (1) a semipermeable wall comprising a cellulose ether and a permeability enhancer that, (2) surrounds a compartment containing a beneficial agent and has, (3) a passageway through the wall that connects the exterior of the device with the compartment for dispensing agent from the device.

BACKGROUND OF THE INVENTION

Osmotic dispensing systems for delivering various useful agents to an environment of use are known to the prior art in U.S. Pat. No. 3,845,770 issued to patentee Theeuwes and Higuchi, and in U.S. Pat. No. 3,916,899, issued to the same patentees. The osmotic systems disclosed in these patents are manufactured in the form of osmotic dispensing devices and they comprise a semipermeable wall surrounding a compartment that contains an agent. The wall is permeable to the passage of an external fluid, and it is substantially impermeable to the passage of agent. The osmotic systems have a passageway through the wall that connects the compartment with the exterior of the device for delivering the agent from the device. These devices deliver an agent by imbibing fluid through the wall into the compartment, at a rate determined by the permeability of the wall and the osmotic pressure gradient across the wall, to produce an aqueous solution containing agent that is delivered through the passageway from the device. The devices are effective for delivering, (a) an agent that is soluble in fluid imbibed into the compartment, thereby forming a solution of the agent that is delivered from the device, and also for delivering, (b) an agent that is poorly soluble in fluid and is mixed with an osmotically effective solute that is soluble in fluid imbibed into the device, thereby forming a solution of the solute containing agent in suspension that is delivered from the device.

Osmotic devices having composite walls are described in U.S. Pat. No. 4,077,407, issued to Theeuwes and Ayer. This patent describes osmotic devices having walls formed of a first polymer stabilized with a second polymer, and optionally the wall can contain a dispersant, a plasticizer, or a flux enhancer. The composite wall of these devices are coated from organic solvents. The walls are made as composites for increasing their resistance to hydrolysis in the presence of agents over a wide pH range, for increasing their exclusion towards agents, and for increasing their flux rates.

The prior art osmotic devices described above represent an outstanding advancement in the drug delivery art, and they are useful for delivering innumerable beneficial agents to many environments of use. It will be appreciated by those versed in the delivery art, that improvements can be made in the wall, the usefulness of the devices can be increased, and consequently their applications broadened, if devices are provided having walls possessing desirable permeabilities and formed of biologically acceptable materials applied from nontoxic solvent systems. For example, both the wall and the usefulness of a device would be unexpectedly increased, if (a) an osmotic device is provided with a pharmaceutically acceptable wall comprising a cellulose ether formulation possessing permeability characteristics conducive for delivering agents to biological environments and if, (b) the wall is formed with nontoxic solvent systems that are non-deleterious and innocuous to the biological environment and the atmosphere, and (c) the wall-forming material is particularly resistant to physical or chemical change in the presence of these agents.

OBJECTS OF THE INVENTION

Accordingly, it is an immediate object of this invention to provide an osmotic device for the controlled and continuous dispensing of an active agent over a prolonged period of time, which device is an improvement in the dispensing art.

Another object of the invention is to provide an osmotic device having a wall comprising a plurality of pharmaceutically acceptable wall forming materials that are substantially inert towards agents and solutions thereof.

Another object of the invention is to provide an osmotic device having a wall comprising a multiplicity of wall forming materials that can be manufactured into an osmotic device with non-toxic solvent systems.

Yet another object of the invention is to provide an osmotic device comprising a semipermeable wall formed of a cellulose ether that is non-toxic and insoluble in the digestive system, and can be coated from an alcohol-aqueous system.

Still yet another object of the invention is to provide an osmotic device that possesses from low to high flux rates to fluids, a high degree of exclusion towards agents, and resistance to physical or chemical change in the presence of agents and biological fluids.

Still a further object of the invention is to provide an osmotic dispensing system that can administer a complete pharmaceutical regimen to a human for a particular time period, the use of which requires intervention only for initiation and possibly termination of the regimen.

Yet still a further object of the invention is to provide an osmotic device consisting essentially of a semipermeable wall in which wall properties such as fluid flow-through rates can be controlled and varied to a particular application, and which device can deliver drugs over a prolonged period of time and thereby eliminate the necessity for taking multiple doses of drugs.

Other objects, features and advantages of the invention will be more apparent to those skilled in the delivery art from the following specification, taken in conjunction with the drawings and the accompanying claims.

SUMMARY OF THE INVENTION

This invention concerns an osmotic device useful for dispensing an active agent to an environment of use. The device is comprised of a wall surrounding a compartment and it has a passageway in the wall communicating with the exterior of the device. The compartment contains an agent that exhibits an osmotic pressure gradient across the wall against an external fluid, or it contains a mixture of an agent and an osmotically effective compound that exhibits an osmotic pressure gradient across the wall against the fluid. The wall is comprised of a wall forming formulation comprising a cellulose ether and a permeability enhancer, with the resultant semipermeable wall permeable to the external fluid, substantially impermeable to agent, compounds and solutions thereof. Agent is dispensed from the device by fluid being imbibed through the wall into the compartment to dissolve agent or the compound and produce in either embodiment a solution that is released under osmotic pressure through the passageway at a controlled and continuous rate over a prolonged period of time. The invention also concerns the use of non-toxic solvent system for manufacturing the osmotic device.

BRIEF DESCRIPTION OF THE DRAWINGS

In the drawings, which are not drawn to scale, but are set forth to illustrate various embodiments of the invention, the figures are as follows.

In the drawings and in the specification, like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
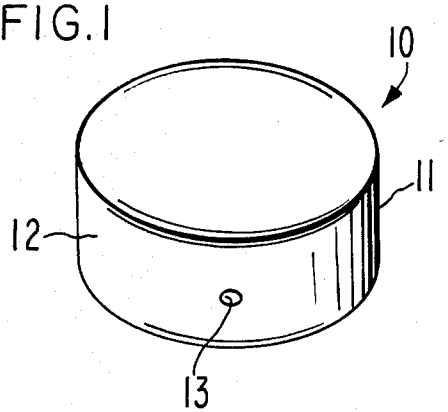
FIG. 1 is a view of an osmotic device designed for orally administering a beneficial agent in the gastrointestional tract.

Turning now to the drawings in detail, which are examples of various osmotic delivery devices provided by the invention, and which examples are not to be considered as limiting, one example of an osmotic device is indicated in FIG. 1 by the numeral 10. In FIG. 1, osmotic device 10 comprises a body 11 having a wall 12 and a passageway 13 in wall 12. Passageway 13 connects the interior with the exterior of the device.

Figure 2:
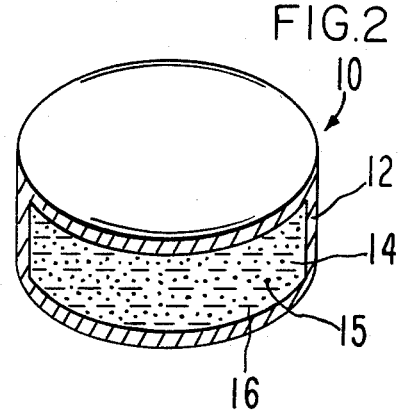
FIG. 2 is a view of the osmotic device of FIG. 1 seen in opened-section for illustrating the structure of the device including the wall and the compartment.

In FIG. 2, device 10 of FIG. 1 is seen in opened-section with a portion of wall 12 removed for illustrating the internal structure of device 10. Device 10 comprises wall 12 that surrounds and defines an internal compartment 14. Passageway 13, seen in FIG. 1, connects compartment 14 with the exterior of device 10. Compartment 14 contains an agent formulation 15 that in one embodiment (a) consists of a beneficial agent that is soluble in an external fluid 16 that enters compartment 14 and it exhibits an osmotic pressure gradient across wall 12 against the external fluid, or in another embodiment (b) agent formulation 15 consists of an agent that has limited solubility or is substantially insoluble in external fluid 16 and is mixed with an osmotically effective compound that is soluble in external fluid and exhibits an osmotic pressure gradient across the wall against the external fluid. Compartment 14 can contain also other compounds such as a surfactant for wetting the agent, and a non-toxic dye for identifying the agent or for making release of agent visible to the eye.

Wall 12 of osmotic device 10 is a composite comprising at least two wall forming materials blended to form a semipermeable wall 12. Composite wall 12 is (a) substantially impermeable to the passage of an external fluid, (b) substantially impermeable to the passage of agent 15 and other compounds housed in compartment 14, (c) substantially inert in the presence of agent, compound, and solutions thereof, (d) maintains its physical and chemical integrity in the environment of use during the dispensing of active agent, and (e) is non-toxic and made with non-toxic solvents. A detailed description of wall forming materials, agents, compounds, and solvents used for the purpose of the invention appear later in the specification.

In operation in the environment of use, device 10 releases agent formulation 15 housed in compartment 14 by fluid being imbibed into compartment 13 in a tendency towards osmotic equilibrium at a rate controlled by the permeability of wall 12 and the osmotic pressure gradient across wall 12 to continuously dissolve agent formulation 15 which is osmotically pumped from device 10 through passageway 13 at a controlled and continuous rate over a prolonged period of time. Device 10, in another embodiment, releases agent 15 that has limited solubility in the fluid and is mixed with an osmotically effective compound by fluid being imbibed through wall 12 into compartment 14 in a tendency towards osmotic equilibrium at a rate controlled by the permeability of wall 12 and the osmotic gradient across wall 12 to continuously dissolve the osmotic effectively compound to form a solution containing agent which is pumped from device 10 through passageway 13 at a controlled and continuous rate over a prolonged period of time.

Device 10 of FIGS. 1 and 2 can be made in many embodiments including the presently preferred embodiment for oral use, that is, for releasing in the gastrointestional tract either a locally or systemically acting therapeutic agent over a prolonged period of time. Oral device 10 can have various conventional shapes and sizes such as round with a diameter of 3/16 inch to ⅜ inch, or more, or it can be shaped like a capsule having a range of sizes from triple zero to zero, and from 1 to 8. In these forms, device 10 can be adapted for administering therapeutic agents to animals, including warm-blooded mammals, humans, avians, reptiles and pisces.

Figure 3:
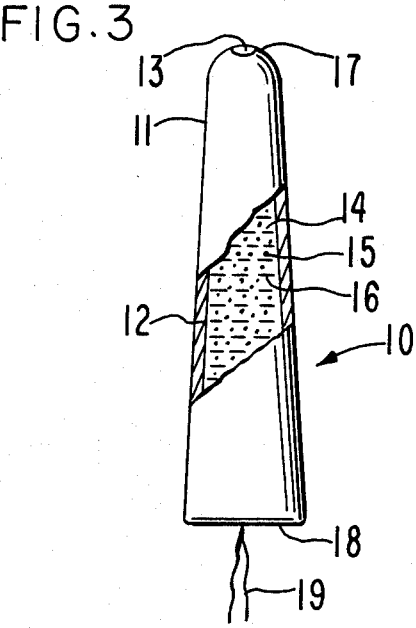
FIG. 3 is a perspective view of another embodiment of the invention comprising a device shaped for delivering a beneficial agent to the ano-rectal and vaginal passageways.

FIG. 3 illustrates another embodiment of the invention designed for easy insertion and prolonged retention in a body passageway, such as a vagina or an ano-rectal canal. Device 10 of FIG. 3 has an elongated, self-sustaining shape with a rounded lead end 17, a trailing end or base 18, optionally equipped with strings 19 for easily removing device 10 from a body passageway, not shown. Device 10 is structurally identical with device 10 as described above and it operates in a like manner.

Figure 4:
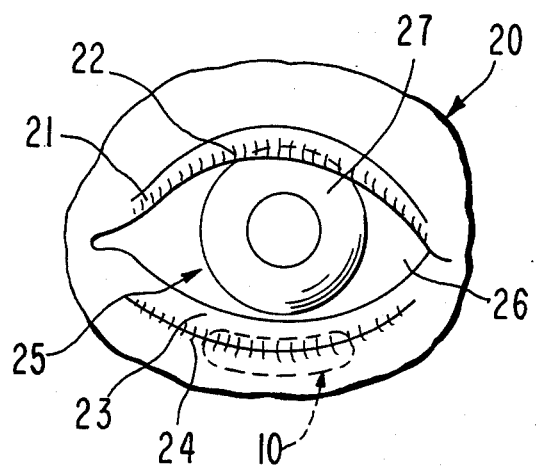
FIG. 4 is a front view of the human eye illustrating an osmotic ocular device, sized and shaped as an ocular insert in operative position in the environment of use; and, FIG. 5 is a graph that depicts the cumulative amount of agent released from an osmotic system over time.

In FIG. 4, an osmotic device 10, manufactured as an ocular insert, is seen in an eye 20 for administering an ocular acceptable drug at an osmotically metered dosage rate thereto. In FIG. 4, eye 20 comprises an upper eyelid 21 with eyelashes 22 and a lower eyelid 23 with eyelashes 24. Eye 20 is comprised of an eyeball 25 covered for the greater part by a sclera 26 and at its center area by cornea 27. Eyelids 21 and 23 are lined with an epithelial membrane or palpebral conjunctiva, and sclera 26 is lined with a bulbar conjunctiva that covers the exposed surface of eyeball 25. Cornea 27 is covered with a transparent epithelial membrane. The portion of the palpebral conjunctiva which lines upper eyelid 21 and the underlying portion of the bulbar conjunctiva defines an upper cul-de-sac, while that portion of the palpebral conjunctiva which lines lower eyelid 23 and the underlying portion of the bulbar conjunctiva define a lower cul-de-sac. Osmotic insert 10 is seen in broken lines in the lower cul-de-sac and it is held in place by the natural pressure of lower eyelid 23. Insert 10 contains an ophthalmic drug for release to eye 20 at a controlled and continuous rate over a prolonged period of time. Ocular insert 10, as manufactured according to the principles described herein, can have any geometric shape that fits comfortably in the cul-de-sac. Typical shapes include ellipsoid, bean, banana, circular, ring, rectangular, doughnut, crescent, and half-ring shaped inserts. In cross-section the insert can be doubly convex, concavo-convex, rectangular and the like, as the insert in use tends to conform to the shape of the eye. The dimensions of an ocular insert can vary widely with the lower limits governed by the amount of drug to be administered to the eye as well as the smallest sized insert that can be placed in the eye. The upper limits on the size of the insert is governed by the space limitations in the eye consistent with comfortable retention in the eye. Satisfactory inserts can have a length of 2 to 20 millimeters, a width of 1 to 15 millimeters, and a thickness of 1 to 4 millimeters. The ocular insert can contain from 0.15 micrograms to 300 milligrams of drug, or more for release over time.

FIGS. 1 through 4 are illustrative of various devices that can be made according to the invention, and these devices are not to be construed as limiting, as the devices can take a wide variety of shapes, sizes and forms for delivering beneficial agents to the environment of use. For example, the devices can include buccal, implant, artificial gland, cervical, nasal, intrauterine, and blood delivery devices. The devices also can be sized, shaped, structured, and adapted for delivering an active agent in aquariums, fields, factories, hot houses, hospitals, farms, transportation means, naval means, veterinary clinics, nursing homes, sickrooms, chemical reactions, and the like.

DETAILED DESCRIPTION OF THE INVENTION

In accordance with the practice of this invention, it has now been found osmotic device 10 can be manufactured with an improved wall 12 comprising at least two wall forming materials that act together to yield a semipermeable wall that operates like a wall formed of a single material. Wall 12 comprises a primary wall forming material consisting of a selectively permeable cellulose ether that is permeable to the passage of fluid and substantially impermeable to the passage of agents and compounds. The presently preferred cellulose ether is ethyl cellulose. Ethyl cellulose is a non-toxic polymer, insoluble in water, essentially insoluble in the digestive system, soluble in the organic solvent ethyl alcohol and in solvent systems consisting essentially of alcohol and water. A presently more preferred ethyl cellulose has an ethoxy group degree of substitution of 1.5 to 3 about 40 to 50% ethoxy content; and a viscosity range of 7 to 100 centipose, or higher. In accompanying Table 1 immediately below, one of the useful properties of ethyl cellulose is compared with the same property of cellulose acetate. In the Table, the elastic moduli of ethyl cellulose and cellulose acetate membranes in saturated aqueous solution of the drug theophylline olamine are compared and the result is set forth in the Table. The results demonstrate the exceptional inertness of ethyl cellulose having an ethoxy content of 48.0–49.5% and a viscosity of 100 cps compared with cellulose acetate having an acetyl content of 39.8% and a viscosity of 3800 cps, and that ethyl cellulose is more inert as demonstrated by a lack of any change in its modulus while cellulose acetate by contrast undergoes a large modulus reduction, which indicates an interaction with the drug. In Table 1, all the membranes were conditioned in the respective medias for 45 hours at 37° C. prior to testing, and the pH of the saturated drug solution was 9.0.

TABLE 1

| Membrane Composition | Modulus in Water (PSI) | Modulus in Saturated Drug (PSI) | % Δ |
|---|---|---|---|
| Cellulose Acetate | $2.1 \times 10^5$ | 4813 | −98 |
| Ethylcellulose | $1.8 \times 10^5$ | $1.8 \times 10^5$ | 0 |

Semipermeable wall 12 contains also a wall forming pharmaceutically acceptable water insoluble polymer, or a pharmaceutically acceptable water soluble polymer or a pharmaceutically acceptable water soluble agent. These polymers or agents, in either embodiment, are permeability enhancers that aid in regulating the passage of fluid into the osmotic device. Representative of water soluble polymers and agents for the present purpose are a member selected from the group consisting essentially of water soluble polymer such as celluloses represented by hydroxypropyl cellulose, hydroxypropyl methylcellulose, hydroxyethyl cellulose, ethyl methylcellulose, methylcellulose, acrylics including polyacrylic acid, polyethyl methacrylate, polymethyl methacrylate, pyrrolidones including polyvinyl pyrrolidone, alkylated vinylpyrrolidone polymers, poly(vinylpyrrolidone/vinyl acetate)copolymers, vinylpyrrolidone/dimethylamino-ethylmethacrylate copolymers, maleic acid polymers such as monobutyl ester of poly(methyl vinylether/maleic acid), monoethyl ester of poly(methylvinyl ether/maleic acid), poly(methyl vinylether/maleic anhydride)copolymer, polyvinyl alcohol hydrolyzed 75 to 85%, water soluble agents such as polyethylene glycol, polyethylene oxide, guar gum, gum arabic, dextran, citric acid, triethyl citrate, acetyltriethyl citrate, sucrose, fructose, glycerin, triacetin, and the like.

Representative of water insoluble, alcohol-water soluble or dispersable polymers are a member selected from the group consisting essentially of carboxy polymers, blended with hydroxy polymers and insolubilized by curing with an energy source. The presently preferred carboxy polymers is carboxyvinyl polymer, also known as carboxypolymethylene, a polymer consisting of acrylic acid crosslinked with polyallyl sucrose as described in U.S. Pat. Nos. 2,798,053 and 2,909,462 as sold under the trademark Carbopol. The presently preferred hydroxy polymer is hydroxypropyl cellulose sold under the trademark Klucel. The presently preferred ratio of these is polyhydroxy:polycarboxy 4:1. Other carboxy polymers can optionally be used including poly(methyl vinylether maleic anhydride), ethylene/acrylic acid copolymer, ethylene maleic acid anhydride copolymers, methacrylic acid ethylacrylate copolymers, and the like. Other hydroxy polymers include hydroxyethyl cellulose, hydroxyethyl starch, poly(hydroxyethyl methacrylate), hydroxybutyl methylcellulose, and the like. Other representative water-insoluble, alcohol-water soluble polymers are cellulose nitrate, polyalkyds, polyvinyl acetal, polyvinyl butyral, vinyl alcohol-vinyl acetate copolymer, vinyl alcohol-vinyl butyral copolymer, polyethylacrylate and the like.

The energy source used in this process can be heat, electromagnetic radiation such as ultraviolet light, microwave irradiation, heat with irradiation, heat with forced air, vacuum treatment, ultrasonic vibration, and the like. The presently preferred energy source is heat with vaccum which serves to insolubilize the polymer by Equation 1.

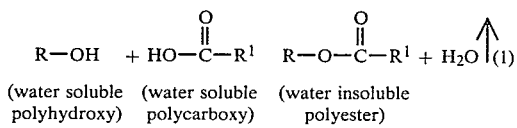

(water soluble polyhydroxy) (water soluble polycarboxy) (water insoluble polyester)

wherein R represents a hydroxy polymer backbone, and $R^1$ represents a carboxy polymer backbone. The product of this reaction is the ester crosslinked polymer which is hydrophilic and substantially insoluble in biological fluids. The water byproduct is continuously removed as the reaction proceeds.

Optionally, water insoluble agents can be included as plasticizers into the wall to increase its flexibility. Agents in this group include tributyl citrate, acetyltributyl citrate, acetyl-tri-2-ethylhexayl citrate, tributyl sebeccate, castor oil, castor oil fatty acids, mono-, di-, and triglycerides, and oils such as corn, cottonseed, peanut and soya.

The term composite as used herein means the wall is comprised of a blend of these materials that act together to form the operative semipermeable wall of the device. The amount of the (a) primary wall forming cellulose ether present in the wall is about 20 to 90 wt%, weight percent, the amount of (b) water soluble hydrophilic polymer or hydrophilic agent is about 10 to 50 wt%, the amount of (c) water insoluble, hydrophilic polymer is about 10 to 80 wt%, or, (d) the composite wall consists of (a) and a mixture of (b) and (c), with the semipermeable composite wall comprising 100 wt%. Polymers (b) and (c) are formulated into the semipermeable wall to (e) provide a more uniform rate of release, to (f) provide a more complete release of the active agent, to (g) impart physical strength and prolong the life of the wall, and to (h) provide a means for adjusting the permeability of the wall by selecting the ratio of (a) to (b) or (c), or the ratio of (a) to (b) and (c). The permeability change is effected by corresponding change in the proportions and it is reproducible. The polymers are known to the art in *Handbook of Common Polymers*, by Scott and Roff, 1971, published by CRC Press; in *Materials Handbook*, by Brady and Clauser, 1977, published by McGraw-Hill; and in *Handbook of Plastics and Elastomers*, by Harper, 1975, published by McGraw-Hill.

Exemplary solvent systems useful for manufacturing the semipermeable wall of the osmotic device are in a presently preferred embodiment non-toxic solvent systems. These systems include ethyl alcohol, and blends of ethyl alcohol with water such as ethanol, ethanol-water (95:5 wt:wt), ethanol-water (90:10), ethanol-water (70:30), and the like.

The expression passageway as used herein comprises means and methods suitable for releasing the useful agent from the device. The expression includes aperture, orifice, or bore through the wall formed by mechanical procedures, or by eroding an erodible element, such as a gelatin plug, in the environment of use. A detailed description of osmotic passageways and the maximum and minimum dimensions for a passageway are disclosed in U.S. Pat. Nos. 3,845,770 and 3,916,899.

The osmotic devices of the invention are manufactured by standard techniques. For example, in one embodiment the agent and other ingredients that may be housed in the compartment and an optional solvent are mixed into a solid, semi-solid or gel form by conventional methods such as ballmilling, calendering, stirring or rollmilling, the solvent evaporated, and then pressed into a preselected shape. The wall forming the device can be applied by molding, spraying, dipping, or pan coating the pressed shape into wall forming materials. In another embodiment a wall can be cast into a film, shaped to the desired dimensions, sealed to define a hollow compartment that is filled with agent, and then closed with a passageway formed in the wall. The device also can be manufactured with an empty compartment that is filled through the passageway. High frequency electronic techniques can be used to provide devices with wall having clean edges. Another, and presently preferred technique that can be used is the air suspension procedure. This procedure consists in suspending and tumbling the pressed agent and other ingredients in a current of air and the wall forming compositions until the wall is applied to the agent. The air suspension procedure is described in U.S. Pat. No. 2,799,241; in *J. Am. Pharm. Assoc.*, Vol. 48, pages 451 to 459, 1959; and ibid, Vol. 49, pages 82 to 84, 1960. Other standard manufacturing procedures are described in *Modern Plastics Encyclopedia*, Vol. 46, pages 62 to 70, 1969; in *Pharmaceutical Sciences*, by Remington, 14th Ed., pages 1626 to 1678, 1970; and in U.S. Pat. No. 4,236,525 issued to patentees Swanson and Edgren.

The expressions useful agent and beneficial agent, as used herein broadly include any compound that can be delivered from the device to produce a beneficial and useful result. The active agents include pesticides, herbicides, germicides, biocides, algicides, rodenticides, fungicides, insecticides, anti-oxidants, plant growth promoters, plant growth inhibitors, preservatives, disinfectants, sterilization agents, catalysts, chemical reactants, fermentation agents, sex sterilants, fertility inhibitors, fertility promoters, air purifiers, micro-organism attenuators, and other beneficial agents.

In the specification and the accompanying claims, the term agent includes drugs, which are the presently preferred agent, and which drugs include any physiologically or pharmacologically active substance that produces a local or systemic effect(s) in animals, which include warm-blooded mammals, humans, primates, household, sport, farm, zoo and laboratory animals, avians, reptiles and pisces. The term physiological as used herein denotes the administration of a drug to produce normal levels and functions. The term pharmacological denotes variations in response to the amount of drug administered to the host. See *Stedman's Medical Dictionary*, 1966, published by Williams and Wilkins, Baltimore, Md. The active drugs that can be delivered include inorganic and organic drugs, without limitations, drugs that act on the central nervous system, depressants, hypnotics, sedatives, psychic energizers, tranquilizers, anticonvulsants, muscle relaxants, antiparkinsons, analgesics, anti-inflammatory, anesthetics, muscle contractants, antimicrobiols, antimalarials, hormonal drugs, contraceptives, sympathomimetics, diuretics, antiparasitics, neoplastics, hypoglycemics, ophthalmics, electrolytes, diagnostics, cardiovascular drugs, and the like.

The drugs can be in various forms such as uncharged molecules, molecular complexes, pharmacologically acceptable salts, such as hydrochlorides, hydrobromides, sulfate, laurylate, palmitate, phosphate, nitrate, borate, acetate, maleate, tartrate, oleate, and salicylate. For acidic drugs, salts of metals, amines, or organic cations, for example quaternary ammonium can be used. Derivatives of drugs such as esters, ethers, and amides which have solubility characteristics suitable for use herein can be used alone, or mixed with other drugs. Also, a drug that is water insoluble can be used in a form that is a water soluble derivative thereof to effectively serve as a solute, and on its release from the device, is converted by enzymes, hydrolyzed by body pH, or converted by other metabolic processes to the original form, or to a biologically active form. The agent can be in the reservoir as a solution, dispersion, paste, creams, particle, granule, emulsion, suspension, or powder. Also, the agent can be mixed with a binder, dispersant, emulsifier, wetting agent, and dyes.

The amount of agent present in the device is preferably initially in excess of the amount that can be dissolved in the fluid that enters the compartment. Under this physical state when the agent is in excess, the device will osmotically operate to give a substantially constant rate of release. The rate of agent release pattern can also be varied by having different amounts of agent in the reservoir to form solutions containing different concentrations of agent for delivery from the device. Generally, the device can house from 10 ng to 2 grams, with individual devices containing for example, 25 ng, 1 mg, 25 mg, 100 mg, 250 mg, 500 mg, 1 g, and the like.

The osmotically effective compounds that can be used for the purpose of the invention include inorganic and organic compounds that exhibit an osmotic pressure gradient across the semipermeable wall against an external fluid. These compounds are used mixed with an agent that has limited solubility in the external fluid with the compound forming a saturated solution containing agent that is osmotically delivered from the device. The phrase limited solubility as used herein means the agent has a solubility of less than 1% by weight in the external fluid. The compounds are used by homogenously or heterogenously mixing the compound, or a mixture of compounds with an agent, either before they are charged into the reservoir, or by self-mixing after they are charged into the reservoir. In operation, these compounds attract fluid into the device producing a solution of compound which is delivered from the device concomitantly transporting undissolved and dissolved agent to the exterior of the device. Osmotically effective compounds useful for the present purpose include magnesium sulfate, magnesium chloride, sodium chloride, lithium chloride, potassium sulfate, sodium carbonate, sodium sulfite, lithium sulfate, potassium chloride, sodium sulfate, potassium acid phosphate, d-mannitol, urea, inositol, tartaric acid, carbohydrates such as raffinose, sucrose, glucose, and mixtures thereof. The compound is initially present in excess and it can be in any physical form such as particle, crystal, pellet, tablet, strip, film, or granule. The osmotic pressure of saturated solutions of various osmotically effective compounds and for mixtures of compounds at 37° C. in water, is listed in Table 2. In the table, the osmotic pressure $\pi$, is in atmospheres, atm. The osmotic pressure is measured in a commercially available osmometer that measures the vapor pressure difference between pure water and the solution to be analyzed, and according to standard thermodynamic principles, the vapor pressure is converted into the osmotic pressure difference. In Table 2, osmotic pressures of from 20 atm to 500 atm are set forth, of course, the invention includes the use of lower osmotic pressures from greater than zero, and higher osmotic pressures than those set forth by way of example in Table 2. For example, in the gastrointestinal tract, the osmotic pressure gradient across the wall in the compartment will be from greater than 0 up to 500 atm per membrane thickness. That is, the osmotic pressure in the compartment will be in excess of 8 atm up to 500 atm. The osmometer used for the present measurements is identified as Model 302B, Vapor Pressure Osmometer, manufactured by the Hewlett Packard Co., Avondale, Pa.

TABLE 2

| OSMOTIC COMPOUND OR MIXTURE | OSMOTIC PRESSURE (atm) |
| --- | --- |
| Lactose-Fructose | 500 |
| Dextrose-Fructose | 450 |
| Urea | 445 |
| Sucrose-Fructose | 430 |
| Mannitol-Fructose | 415 |
| Sodium Chloride | 356 |
| Fructose | 355 |
| Sorbitol | 305 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Mannitol-Sucrose | 170 |
| Sodium Citrate | 165 |
| Sucrose | 150 |
| Citric Acid | 150 |
| Mannitol-Lactose | 130 |
| Dextrose | 82 |
| Potassium Sulfate | 39 |
| Mannitol | 38 |
| Sodium Phosphate Tribasic.12H$_2$O | 36 |
| Sodium Phosphate Dibasic.12H$_2$O | 31 |
| Sodium Phosphate Dibasic.7H$_2$O | 31 |
| Sodium Phosphate Dibasic Anhydrous | 29 |

The following examples are merely illustrative of the present invention, and they should be considered as limiting the scope of the invention in any way, as these examples and other equivalents thereof will become apparent to those versed in the art in the light of the present disclosure, the drawings, and the accompanying claims.

EXAMPLE 1

An oral osmotic therapeutic system for the controlled and continuous release of the beneficial agent indomethacin to the gastrointestinal tract was made as follows: first a drug compartment weighing 280 mg was prepared by blending 37.6 wt% of sodium indomethacin trihydrate, 56.4 wt% of potassium bicarbonate, 3 wt% of polyvinyl pyrrolidone, and 3 wt% of stearic acid for about 30 minutes to yield a uniform mixture. The mixture was then compressed in a conventional Manesty tableting machine using a 5/16 inch diameter punch to produce a compressed drug core having a hardness of about 9 kg.

Figure 5:
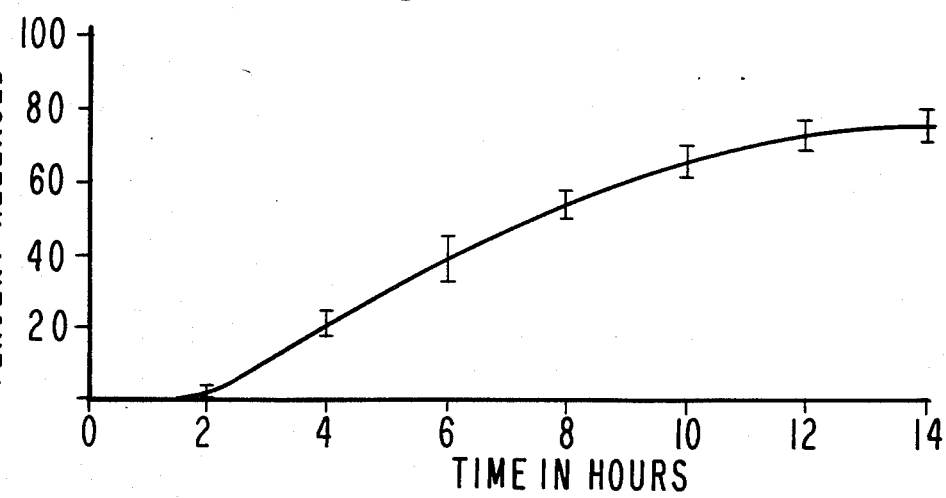

Next, a wall forming composition consisting of 40 wt% ethyl cellulose, 48.0–49.0% ethoxy content, 100 cps, 48 wt% of hydroxypropyl cellulose, and 12 wt% of carboxypolymethylene in an ethanol-water, 95:5, solvent system were placed in a Wurster air suspension machine and the drug cores air coated until they were uniformly coated with the composite, semipermeable wall. A 5 mil passageway was then laser drilled through the composite wall. Finally, the coated drug cores were dried in an oven at 65° C. under vacuum for one day to cure the wall and to produce the osmotic device. The resulting device contained 82.3 mg of indomethacin and it had an average release rate of about 5 mg per hr. over a 14 hour drug release period. The cumulative amount released over time is seen in FIG. 5.

EXAMPLE 2

As in Example 1 except the drying conditions were two days at 55° C. in vacuo.

EXAMPLE 3

An osmotic therapeutic device for the controlled and continuous release in the rectum of the beneficial drug sodium diclofenac is made as follows: first 5.6 wt% of sodium diclofenac, 93.4 wt% of urea, 0.5% wt% of polyethylene glycol 400, and 0.5 wt% of stearic acid are blended to form a homogenous blend, and the composition fed into a tablet press and pressed at 5 to 6 tons pressure. Next, the pressed compositions are coated with a semipermeable wall forming composition comprising 80 wt% of ethylcellulose 48.0–49.5 ethoxy content, 100 cps, 15 wt% of hydroxypropyl methylcellulose and 5 wt% of glycerin, from a solvent system consisting of ethanol-water, (90:10). An air suspension machine is used for coating the semipermeable wall that forms the compartment. A passageway having a diameter of 7.5 mils is laser drilled through the wall of delivering the drug from the device.

EXAMPLE 4

An osmotic therapeutic device for release of a therapeutic agent is prepared by a process provided by the invention for manufacturing the device with wall forming materials that are soluble in an alcohol, or an alcohol-aqueous solvent system, are rendered substantially insoluble by the process of the invention. The process is carried out as follows: first, 235 mg of procainamide hydrochloride is mixed with 5 mg of polyvinyl pyrrolidone and charged into a round mold having a concaved lower surface. The blend is compressed with a $\frac{3}{8}$ inch plunger having a convexed surface under an applied force of $6 \times 10^3$ psi.

Next, the compressed drug is removed from the mold and placed in an air stream containing a wall forming composition. The composition consists of ethyl cellulose 48.0–49.5 ethoxy content, 45 cps, 50 wt%, hydroxypropyl cellulose 40 wt%, and carboxyvinyl polymer 10 wt%, in ethanol-water 70:30, wt:wt, and the drug cores coated with a semipermeable wall to form a drug compartment.

An orifice of 7.5 mil diameter is laser drilled through the semipermeable wall for releasing the drug from the compartment of the device. Then, semipermeable wall surrounding and forming the compartment is cured in vacuo at a temperature range of from 60° to 80° C., preferably at 75° C. for 1 to 7 days, preferably 4 days to provide the device. The final wall is 5 to 10 mil thick and the improved process yield walls sufficiently rigid and substantially insoluble in water.

EXAMPLE 5

An osmotic therapeutic system for the controlled and continuous oral release of the beneficial agent potassium chloride was made as follows: 500 mg potassium chloride plus 5 wt% polyvinyl pyrrolidone plus 1 wt% magnesium stearate were tableted with a $\frac{3}{8}$ inch diameter punch. The wall of the device comprised 70% ethylcellulose having an ethoxy content of 45.0–47.0%, 100 cps, 15% fructose and 15% polyethylene glycol 4000. A 4 mil thick wall was coated from an ethanol-water 82:18, solvent mixture. An exit portal of 10 mil diameter was then laser drilled through the wall.

The novel osmotic device of this invention uses means for obtaining the controlled release in the environment of use while simultaneously maintaining the integrity of the device. While there has been described and pointed out features of the invention as applied to embodiments thereof, those skilled in the art will appreciate that various modifications, changes, additions and omissions in the devices illustrated and described can be made without departing from the spirit of the invention.

I claim:

1. An osmotic delivery system for the controlled dispensing of a useful agent to an environment of use, wherein said system comprises:
   (a) a shaped semipermeable wall permeable to the passage of fluid and substantially impermeable to the passage of an useful agent, said semipermeable wall consisting essentially of an organic solvent soluble cellulose ether and a permeability enhancer selected from the group consisting of an organic solvent soluble carboxypolymethylene, polyvinyl acetal, polyvinyl butyral, polyalkyds, polymethacrylonitrile, vinyl alcohol-vinyl acetate copolymer, and vinyl alcohol-vinyl butyral copolymer, the semipermeable wall surrounding and forming:
   (b) a compartment containing a useful agent formulation that is soluble in an external fluid imbibed through the semipermeable wall into the compartment and exhibits an osmotic pressure gradient across the semipermeable wall against the external fluid; and,
   (c) an osmotic passageway in the wall communicating with the compartment and the exterior of the system for dispensing the agent formulation through the osmotic passageway from the device to the environment of use.

2. The osmotic delivery system for the controlled dispensing of a useful agent according to claim 1, wherein the agent is a drug.

3. The osmotic delivery system for the controlled dispensing of a useful agent according to claim 1, wherein the agent formulation comprises an osmotically effective solute.

4. An osmotic delivery system for the controlled dispensing of a useful agent to an environment of use, wherein said system comprises:
   (a) a shaped semipermeable wall permeable to the passage of an external fluid and substantially impermeable to the passage of a useful agent formulation, comprising an organic solvent soluble cellulose ether and a permeability enhancer selected from the group consisting of an organic solvent soluble carboxypolymethylene, polyvinyl acetal, polyethylene oxide, polyethylene glycol, polyvinyl butyral, polyalkyds, polymethacrylonitrile, vinyl alcohol-vinyl acetate copolymer, vinyl alcohol-vinyl butyral copolymer, and a hydrophilic polyester formed from hydroxy and carboxy polymers, said semipermeable wall additionally contains a member selected from the group of an aqueous soluble polyvinyl alcohol, polyvinyl pyrrolidone, hydroxypropyl cellulose, hydroxypropylmethyl cellulose, methyl cellulose, guar gum, dextran and, the wall surrounding and forming:

(b) a compartment containing a useful agent formulation that is soluble in an external fluid imbibed through the wall into the compartment and exhibits an osmotic pressure gradient across the wall against the external fluid; and, (c) an osmotic passageway in the wall communicating with the compartment and the exterior of the system for dispensing the agent formulation through the passageway from the device to the environment of use.

5. An osmotic delivery system for the controlled dispensing of a useful agent to an environment of use, wherein said system comprises:

(a) a shaped semipermeable wall permeable to the passage of fluid and substantially impermeable to the passage of an useful agent, consisting essentially of an organic solvent soluble cellulose ether and a blend of water soluble polymers, which water soluble polymers on the application of energy used to coat the semipermeable wall of the delivery system, forms a hydrophilic and substantially fluid insoluble polymer in the semipermeable wall on the device, the semipermeable wall containing the insoluble polymer surrounding and forming:

(b) a compartment containing a useful agent formulation that is soluble in an external fluid imbibed through the semipermeable wall into the compartment and exhibits an osmotic pressure gradient across the semipermeable wall against the external fluid; and, (c) an osmotic passageway in the wall communicating with the compartment and the exterior of the system for dispensing the agent formulation through the passageway from the system to the environment of use.

6. An osmotic delivery system for the controlled dispensing of a beneficial agent to an environment of use, wherein the osmotic system comprises;

(a) a shaped wall formed of a semipermeable composition permeable to the passage of an external fluid and substantially impermeable to the passage of an useful agent, consisting essentially of an organic solvent soluble cellulose ether, a polyhydroxy polymer and a polycarboxy polymer, which polyhydroxy polymer and polycarboxy polymer react while coating the wall onto the device to form a hydrophilic fluid permeability enhancing polymer blended within the cellulose ether, said wall surrounding and defining:

(b) a compartment containing a useful agent formulation that is soluble in an external fluid imbibed through the wall into the compartment and exhibits an osmotic pressure gradient across the wall against the external fluid; and, (c) an osmotic passageway in the wall communicating with the compartment and the exterior of the system for dispensing the agent formulation through the wall from the system to the environment of use over a prolonged period of time.

7. An osmotic delivery system for the controlled dispensing of the useful agent to an environment of use, wherein said system comprises:

(a) a shaped semipermeable wall permeable to the passage of fluid and substantially impermeable to the passage of a useful agent formulation, consisting essentially of an organic solvent soluble cellulose ether and a blend of water soluble polymers which water soluble polymers on the application of energy form a hydrophilic and substantially fluid insoluble polymer in the wall, said wall additionally containing a member selected from the group consisting essentially of hydroxyethyl cellulose, ethyl methylcellulose, polyacrylic acid, polyethyl methacrylate, polymethyl methacrylate, polyalkylated polyvinylpyrrolidone, poly(vinylpyrrolidone-vinyl acetate), poly(methyl vinylether maleic acid), poly(methyl vinylether maleic anhydride), polyethylene oxide, gum Arabic, glycerin, sucrose, fructose, and glucose, the semipermeable wall surrounding and forming:

(b) a compartment containing a useful agent formulation that is soluble in an external fluid imbibed through the wall into the compartment and exhibits an osmotic pressure gradient across the wall against the external fluid; and, (c) an osmotic passageway in the wall communicating with the compartment and the exterior of the system for dispensing the agent formulation from the system to the environment of use.

8. An osmotic system for the controlled delivery of a beneficial agent to an environment of use, wherein the system consists essentially of:

(a) a shaped semipermeable wall, consisting essentially of a cellulose ether and a polyethylene glycol, said semipermeable wall permeable to the passage of an external fluid and substantially impermeable to the passage of a useful agent formulation; which wall surrounds and forms:

(b) a compartment for containing a beneficial agent formulation; and, (c) an osmotic passageway in the wall that connects the compartment and the exterior of the system for dispensing the agent formulation through the osmotic passageway from the osmotic system to the environment of use over time.

9. An osmotic system for the controlled delivery of a beneficial agent to an environment of use, wherein the system consists essentially of:

(a) a shaped semipermeable wall consisting essentially of a cellulose ether and a polyethylene oxide, said semipermeable wall permeable to the passage of an external fluid and substantially impermeable to the passage of agent formulation, which semipermeable wall surrounds and forms:

(b) a compartment for containing a beneficial agent formulation; and, (c) an osmotic passageway in the semipermeable wall that connects the compartment and the exterior of the osmotic system for dispensing the agent formulation through the osmotic passageway from the system to the environment of use over time.

* * * * *